(12) United States Patent
Shelokov

(10) Patent No.: US 6,475,219 B1
(45) Date of Patent: Nov. 5, 2002

(54) ANTERIOR VERTEBRAL PROTECTION METHOD AND DEVICE

(76) Inventor: Alexis P. Shelokov, 3308 Greenbrier Dr., Dallas, TX (US) 75225-4817

( * ) Notice: Subject to any disclaimer, the term of this patent is extended or adjusted under 35 U.S.C. 154(b) by 0 days.

(21) Appl. No.: 09/876,794

(22) Filed: Jun. 7, 2001

(51) Int. Cl.$^7$ ............................................... A61B 17/80
(52) U.S. Cl. ..................................... 606/69; 623/17.16
(58) Field of Search ........................... 606/69, 60, 61, 606/53, 70, 73, 74, 75, 76; 623/16.11, 17.11, 17.16

(56) References Cited

U.S. PATENT DOCUMENTS

| | | | |
|---|---|---|---|
| 4,013,078 A | | 3/1977 | Field |
| 5,415,661 A | * | 5/1995 | Holmes |
| 5,437,672 A | | 8/1995 | Alleyne |
| 5,591,169 A | * | 1/1997 | Benoist |
| 5,611,354 A | | 3/1997 | Alleyne |
| 5,645,599 A | * | 7/1997 | Samani |
| 5,681,310 A | | 10/1997 | Yuan et al. |
| 5,868,745 A | | 2/1999 | Alleyne |
| 6,039,763 A | | 3/2000 | Shelokov |
| 6,206,882 B1 | * | 3/2001 | Cohen |

* cited by examiner

*Primary Examiner*—Pedro Philogene
(74) *Attorney, Agent, or Firm*—Randall C. Brown; Haynes and Boone, L.L.P.

(57) ABSTRACT

A flexible shield or apron formed of a biocompatible material is placed between adjacent vertebral bodies and the vessels and body structure anterior of the spine subsequent to the performance of an anterior spinal surgical procedure. The apron is secured to adjacent vertebral bodies by conventional bone fasteners and is provided with a pleat to allow stretching as a consequence of movement between vertebral bodies to which the apron is connected. The apron may be retracted together with vessels it is shielding during a revision surgical procedure while minimizing risks associated with the formation of adhesions or scar tissue.

13 Claims, 2 Drawing Sheets

ANTERIOR VERTEBRAL PROTECTION METHOD AND DEVICE

BACKGROUND OF THE INVENTION

Spinal disorders requiring surgical procedures are well known. The lumbar region of the human anatomy, for example, is a frequent site of spinal disorders which may be corrected by surgical procedures carried out anteriorly of the lumbar vertebrae including, for example, surgical procedures involving disc removal and/or replacement.

In anterior spinal surgical procedures, the initial surgery is through an unscarred and substantially clear path to the surgical site. In revision surgery, however, the path to the surgical site has been scarred and may present certain dangers. With the present technology in spinal surgeries being focused on anterior insertion of intervertebral prostheses, and other anterior surgical procedures, there continue to be concerns about anterior dislocation of prostheses and vertebral structures as well as potential injury to the significant blood vessels located in proximity to the spine.

Accordingly, it has been determined that a need exists for a method of protecting against potential vascular injury in the vicinity of the spine as a consequence of anterior surgical procedures. Moreover, a need has, thus, also developed for a device which may be conveniently interposed the spinal column and, particularly, major blood vessels such as the aorta and the vena cava, so that the vessels are not normally subject to injury as a consequence of a surgical procedure and/or are not subject to the development of adhesions or tissue which may produce complications during revision surgery. It is to these ends that the present invention has been developed.

BRIEF SUMMARY OF THE INVENTION

The present invention provides a method for protecting major vessels and other anatomical parts from complications as a consequence of anterior spinal surgical procedures. In particular, the present invention contemplates a method for protecting major blood vessels, such as the aorta and the vena cava, and providing some protection against anterior dislocation of vertebral bodies adjacent these vessels. The method also minimizes the formation of adhesions or unwanted joining of certain tissues and body structures to each other pursuant to anterior spinal surgery.

Still further, the present invention provides a device operable to minimize the formation of adhesions between blood vessels and vertebral bodies and adjacent tissues which have been subjected to surgical procedures and to minimize adhesion induced complications in anterior vertebral surgical procedures, in particular.

The present invention still further provides a device in the form of a flexible shield or apron adapted to be placed between the spine and major blood vessels adjacent to the spine. In particular, the flexible shield or apron is adapted to be connected to adjacent vertebral bodies, for example, and provided with a fold or pleat to allow flexing or movement as a consequence of movement of the vertebral bodies relative to each other. The shield or apron is preferably formed as a generally rectangular sheet of biocompatible material and may include a radio-opaque locator tab or be otherwise suitably provided with radio-opaque material.

The present invention is particularly useful in connection with surgical procedures associated with the lumbar region of the spine but may be practiced in conjunction with procedures associated with other spinal regions. Those skilled in the art will further appreciate the advantages and superior features of the invention described hereinabove and will recognize other important aspects thereof upon reading the detailed description which follows in conjunction with the drawing.

DETAILED DESCRIPTION OF THE PREFERRED EMBODIMENTS

Figure 1:
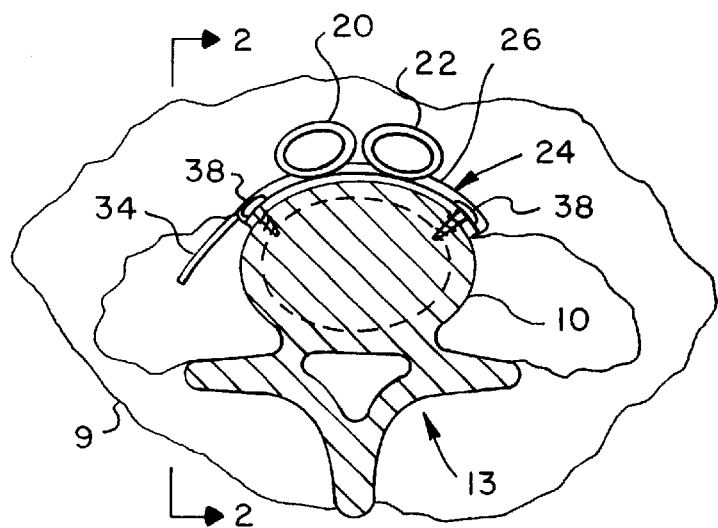
FIG. 1 is a detail section view of the transverse lumbar anatomy, taken generally from the line 1—1 of FIG. 2.

In the description which follows, like elements are marked with the same reference numerals throughout the specification and drawings. In the drawing figures, certain anatomical details may be omitted or shown somewhat schematically in the interest of clarity.

Figure 2:
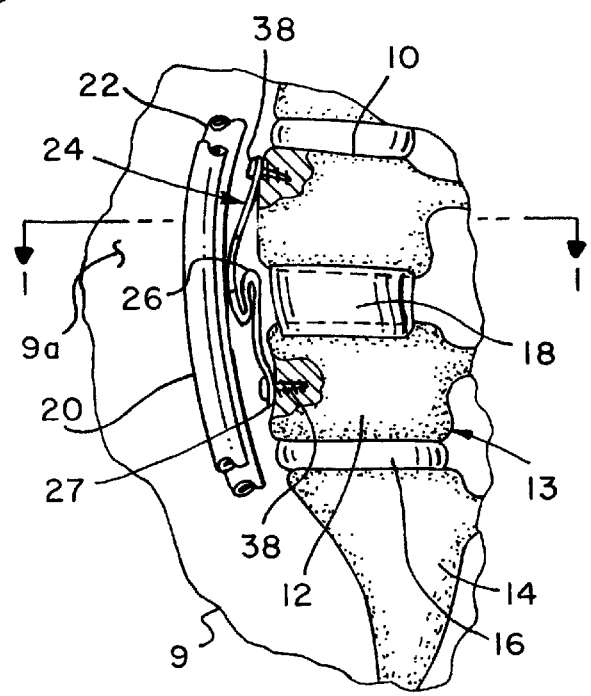
FIG. 2 is a longitudinal detail view taken generally from the line 2—2 of FIG. 1.

Referring to FIGS. 1 and 2, there is illustrated certain details of the lumbar anatomy of a human being 9 including, for example, vertebral bodies 10, 12 and 14 of the spine or spinal column 13, FIG. 2, an intervertebral disc 16 between body 12 and body 14 and a surgical prosthesis 18 interposed vertebral bodies 10 and 12. The prosthesis 18 may be of the type disclosed and claimed in my U.S. Pat. No. 6,039,763, issued on Mar. 21, 2000.

FIGS. 1 and 2, illustrate the normal location of large blood vessels in the vicinity of the spine 13, namely the aorta 20 and the vena cava 22. These vessels are located anterior of the spine 13 and must be retracted during spinal surgery, such as a disc removal or disc prosthesis installation. In order to minimize the development of adhesions between the vertebral bodies 10 and 12 and the vessels 20 and 22, as a consequence of invasive surgical procedures in the vicinity thereof, and to minimize any adverse effects from possible anterior dislocation of the vertebral bodies 10 and 12 or the prosthesis 18, a device 24 in accordance with the invention is shown interposed the vertebral bodies 10 and 12 and the vessels 20 and 22.

Figure 3:
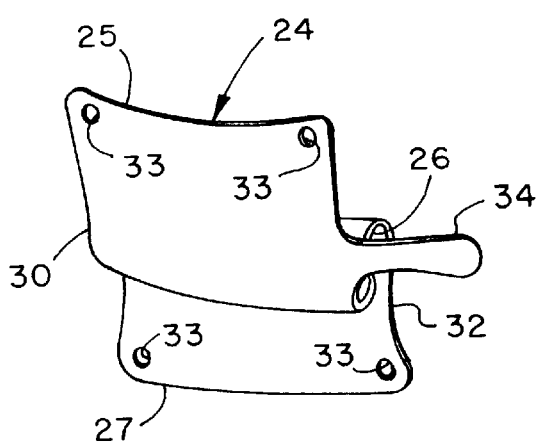
FIG. 3 is a perspective view of the vessel protection device or apron of the present invention.

Referring also to FIG. 3, the device 24 is characterized as a flexible, relatively thin, generally rectangular shield or apron which may be formed of a material sufficiently flexible enough as to provide a double reverse overlapping bend or pleat 26 formed therein, and generally formed intermediate upper and lower edges 25 and 27 of the device. Pleat 26 preferably extends between longitudinal side edges 30 and 32 of the device 24. Suitable fastener receiving holes 33 are preferably disposed adjacent the corners of the device 24, as shown. Moreover, a tab 34, FIG. 3, is provided projecting laterally from side edge 32 of the device 24 and is formed of a radio-opaque material or is treated to be radio-opaque to aid in locating the device once it is in its working position.

Figure 4:
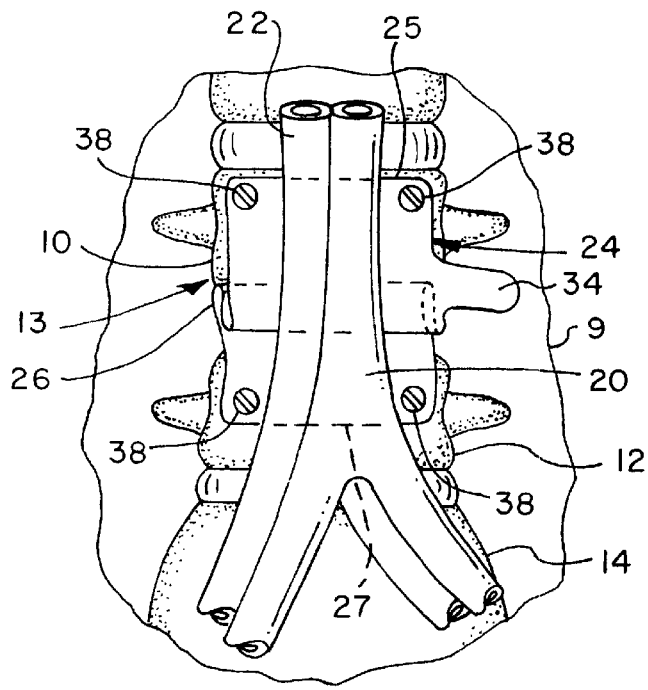
FIG. 4 is a detail view taken from a point anterior of the spine and showing the location of the vessel protecting device or apron in a working position corresponding generally to the position of the device shown in FIGS. 1 and 2.

FIGS. 1, 2 and 4 show the device or apron 24 in its working position extending between vertebral bodies 10 and 12 and secured thereto, respectively, as shown in the drawing figures. Suitable bone fasteners 38 may be extended through the fastener receiving openings 33 and secured to the vertebral bodies 10 and 12, as shown. The fasteners 38 may be conventional fastening elements used in fixing devices to spinal bone structure.

The shield or apron 24 may be fabricated of a flexible, biocompatible or subdermal implant material, such as Silastic brand silicone rubber and similar organosiloxane polymers. Preferably, the dimensions of the device 24 include an overall length between edges 25 and 27 of about 7.0 cm, an overall width between edges 30 and 32 of about 5.0 cm and a thickness of about 0.04 cm to 0.20 cm. Other biocompatible materials and dimensions may be suitable for the apron 24.

In accordance with the method of the invention, subsequent to the performance of an anterior surgical procedure on the spine 13, the device 24 is attached to adjacent vertebrae, preferably as indicated in the drawing figures, by securing the top edge 25 to the vertebral body 10 with fasteners 38 and securing the bottom edge 27 to another vertebral body, such as the vertebral body 12, also with fasteners 38. Preferably enough slack is provided in the device 24 to accommodate movement of the vertebral bodies 10 and 12 with respect to each other. Such slack is conveniently provided by the fold or pleat 26 between the edges 25 and 27.

After attachment of the device 24 to the spine 13 in the manner illustrated and described, the vessels 20 and 22 are allowed to resume their normal position adjacent the spine without fear of injury to the vessels or the development of adhesions and with minimal scar tissue developing. Moreover, the shield or apron 24 also protects at least a portion of the spine 13 from possible anterior dislocation. If a replacement disc 18 has been inserted between the vertebral bodies 10 and 12, for example, as shown, or if certain other surgical procedures were carried out in the vicinity of the vertebral bodies 10 and 12, including implants with any protrusions, the device 24 is operable to minimize dislocations and protect the vessels 20 and 22.

Figure 5:
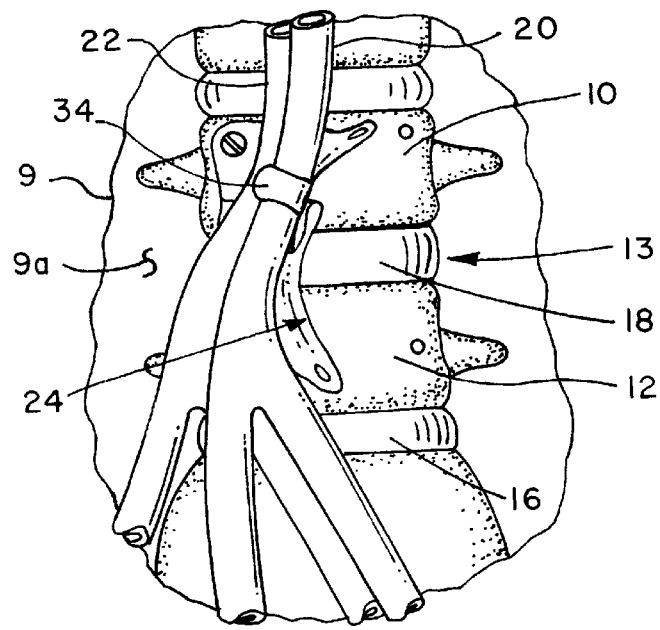
FIG. 5 is a view showing displacement of blood vessels and the device during revision surgery.

In the event that revision surgery is needed, the vessels 20 and 22 may be retracted, upon reentering the body cavity 9a, FIGS. 1, 2 and 5, anterior of the spine 13 and retracting the vessels 20 and 22, as well as the device 24, to provide access to the spine elements including the vertebral bodies 10 and 12 and the replacement disc 18, if needed. The process of performing a revision surgical procedure in the vicinity of a previous procedure, which would otherwise have resulted in the formation of adhesions or dangerous scar tissue, may enjoy the benefits of the present invention. Moreover, placing the device or apron 24 generally as shown and described may be carried out for other anterior invasive procedures in the vicinity of the spine 13 to prevent the subsequent adverse effects of such procedures, as described hereinabove.

Although preferred embodiments of the invention have been described in detail hereinabove, those skilled in the art will appreciate that various substitutions and modifications may be made without departing from the scope and spirit of the appended claims.

What is claimed is:

1. A method for protecting one or more blood vessels disposed anterior of a human being's spine subsequent to an anterior surgical procedure on or in the vicinity of said spine, comprising the step of:
    placing a flexible apron adjacent said spine and interposed said spine and said vessels after the performance of said procedure on said spine, wherein said apron allows relative movement of adjacent vertebral bodies of said spine and minimizes at least one of injury to said vessels, the formation of adhesions or adverse scar tissue and anterior dislocation of portions of said spine.

2. The method set forth in claim 1 including the step of:
    attaching part of said apron to an element of said spine and attaching another part of said apron to another element of said spine.

3. The method set forth in claim 1 including the step of:
    forming a pleat in said apron between upper and lower edges of said apron.

4. The method set forth in claim 1 including the step of:
    providing said apron with a radio-opaque part for identifying and locating said apron via radiography.

5. The method set forth in claim 1 including the step of:
    retracting said vessels and said apron away from said spine during a revision procedure to gain access to a portion of said spine covered by said apron.

6. The method set forth in claim 1 including the step of:
    providing said apron to be formed of one of silicone rubber, organosiloxane polymers and subdermal implant materials.

7. The method set forth in claim 6 including the step of:
    providing said apron to have a thickness of about 0.04 cm to 0.20 cm.

8. A method for protecting vessels disposed anterior of a human being's spine subsequent to an anterior surgical procedure on said spine, comprising the steps of:
    providing a flexible apron formed of a biocompatible material;
    placing said apron adjacent said spine and interposed said spine and said vessels after the performance of said procedure;
    attaching a first part of said apron to a first vertebral body of said spine and attaching a second part of said apron spaced from said first part to a second vertebral body of said spine, wherein said apron allows relative movement of said first vertebral body and said second vertebral body of said spine and minimizes a chance of injury to said vessels upon completion of said procedure.

9. The method set forth in claim 8 including the step of:
    forming a pleat in said apron between said first part and said second part.

10. The method set forth in claim 8 including the step of:
    providing said apron with a radio-opaque part for identifying and locating said apron via radiography.

11. The method set forth in claim 8 including the step of:
    retracting said vessels and said apron away from said spine during a revision procedure to gain access to a portion of said spine previously covered by said apron.

12. A flexible apron for placement between adjacent vertebral bodies and major blood vessels subsequent to performance of an anterior surgical procedure, said apron comprising:
    a flexible member formed of a material selected from a group consisting of silicone rubber, organosiloxane polymers and subdermal implant materials and having a thickness of about 0.04 cm to 0.20 cm, said apron including plural points of attachment for attaching said apron to spaced apart vertebral bodies, wherein said apron allows relative movement of said spaced apart vertebral bodies.

13. The flexible apron set forth in claim 12 including:
    a pleat formed in said apron between said points of attachment.

* * * * *